(12) United States Patent
Alagia et al.

(10) Patent No.: US 11,471,607 B2
(45) Date of Patent: Oct. 18, 2022

(54) DOSE SENSING MECHANISM IN A MEDICATION DELIVERY DEVICE

(71) Applicant: Eli Lilly and Company, Indianapolis, IN (US)

(72) Inventors: Nicola Antonio Alagia, Desio (IT); Roy Howard Byerly, Indianapolis, IN (US); Rossano Claudio Massari, Lissone (IT); Russell Wayne Perkins, Carmel, IN (US)

(73) Assignee: Eli Lilly and Company, Indianapolis, IN (US)

( * ) Notice: Subject to any disclaimer, the term of this patent is extended or adjusted under 35 U.S.C. 154(b) by 521 days.

(21) Appl. No.: 16/321,527

(22) PCT Filed: Aug. 4, 2017

(86) PCT No.: PCT/US2017/045419
§ 371 (c)(1),
(2) Date: Jan. 29, 2019

(87) PCT Pub. No.: WO2018/031390
PCT Pub. Date: Feb. 15, 2018

(65) Prior Publication Data
US 2019/0160229 A1 May 30, 2019

Related U.S. Application Data

(60) Provisional application No. 62/374,202, filed on Aug. 12, 2016.

(51) Int. Cl.
*A61M 5/00* (2006.01)
*A61M 5/315* (2006.01)
*A61M 5/24* (2006.01)

(52) U.S. Cl.
CPC .......... *A61M 5/31551* (2013.01); *A61M 5/24* (2013.01); *A61M 5/31585* (2013.01);
(Continued)

(58) Field of Classification Search
CPC .......... A61M 5/31551; A61M 5/31585; A61M 5/31555; A61M 5/31568
See application file for complete search history.

(56) References Cited

U.S. PATENT DOCUMENTS

| 685,091 A | 10/1901 | Becton |
| 1,625,035 A | 4/1927 | Lilly |

(Continued)

FOREIGN PATENT DOCUMENTS

| EP | 0338806 | 10/1989 |
| EP | 0498737 | 8/1992 |

(Continued)

OTHER PUBLICATIONS

Eli Lilly and Company, Technical Dossier for the HumaPen® Pen-Injector Family, Aug. 15, 2000, pp. 1 and 10-25 provided.
(Continued)

*Primary Examiner* — Nathan R Price
*Assistant Examiner* — Tania Ismail
(74) *Attorney, Agent, or Firm* — Arthur C.H. Shum

(57) ABSTRACT

Medication delivery devices, sensing systems, and methods are disclosed for determining the relative axial and rotational movements of its members to determine the amount of a dose set and/or delivered by the medication delivery device. A sensing system comprises a barrel sensor system (100), a drive sleeve sensor system (130), and/or an axial sensor system (140). The barrel sensor system (100) is for detecting the absolute relative angular position of the barrel relative to the housing during dose setting. The drive sleeve sensor system (130) is for detecting the absolute relative angular
(Continued)

position of the drive sleeve relative to the housing during dose delivery. The axial sensor system (140) is for detecting the relative axial positions of the dose dial relative to the housing during dose setting and delivery. A controller receives outputs from the sensor systems corresponding to the absolute relative positions to determine the actual amounts of dose set and delivered.

14 Claims, 3 Drawing Sheets

(52) U.S. Cl.
CPC ..... *A61M 5/31555* (2013.01); *A61M 5/31568* (2013.01); *A61M 2005/3152* (2013.01); *A61M 2205/3317* (2013.01); *A61M 2205/3327* (2013.01); *A61M 2205/3576* (2013.01); *A61M 2205/50* (2013.01)

(56) References Cited

U.S. PATENT DOCUMENTS

| | | |
|---|---|---|
| 2,853,586 A | 9/1958 | Vercesi |
| 3,399,368 A | 8/1968 | Elliott et al. |
| 3,723,061 A | 3/1973 | Stahl |
| 4,315,252 A | 2/1982 | Tagami |
| 4,486,891 A | 12/1984 | Kimoto et al. |
| 4,529,401 A | 7/1985 | Leslie et al. |
| 4,552,055 A | 11/1985 | Foxwell |
| 4,592,745 A | 6/1986 | Rex et al. |
| 4,865,591 A | 9/1989 | Sams |
| 4,883,472 A | 11/1989 | Michel |
| 4,931,041 A | 6/1990 | Faeser |
| 5,279,586 A | 1/1994 | Balkwill |
| 5,418,362 A | 5/1995 | Lusby et al. |
| 5,509,905 A | 4/1996 | Michel |
| 5,536,249 A | 7/1996 | Castellano et al. |
| 5,569,212 A | 10/1996 | Brown |
| 5,582,598 A | 12/1996 | Chanoch |
| 5,593,390 A | 1/1997 | Castellano et al. |
| 5,626,566 A | 5/1997 | Petersen et al. |
| 5,628,309 A | 5/1997 | Brown |
| 5,674,204 A | 10/1997 | Chanoch |
| 5,688,251 A | 11/1997 | Chanoch |
| 5,691,646 A | 11/1997 | Sasaki |
| 5,704,922 A | 1/1998 | Brown |
| 5,728,074 A | 3/1998 | Castellano et al. |
| 5,743,889 A | 4/1998 | Sams |
| 5,820,602 A | 10/1998 | Kovelman et al. |
| 5,827,232 A | 10/1998 | Chanoch et al. |
| 5,920,198 A | 7/1999 | Suzuki et al. |
| 5,921,966 A | 7/1999 | Bendek et al. |
| 5,925,021 A | 7/1999 | Castellano et al. |
| 5,938,642 A | 8/1999 | Burroughs et al. |
| 5,954,700 A | 9/1999 | Kovelman |
| 5,957,896 A | 9/1999 | Bendek et al. |
| 5,961,496 A | 10/1999 | Nielsen et al. |
| 6,001,089 A | 12/1999 | Burroughs et al. |
| 6,004,297 A | 12/1999 | Steenfeldt-Jensen et al. |
| D425,990 S | 5/2000 | Gravel et al. |
| 6,068,615 A | 5/2000 | Brown et al. |
| 6,080,090 A | 6/2000 | Taylor et al. |
| 6,110,152 A | 8/2000 | Kovelman |
| 6,192,891 B1 | 2/2001 | Gravel et al. |
| 6,221,046 B1 | 4/2001 | Burroughs et al. |
| 6,221,053 B1 | 4/2001 | Walters et al. |
| 6,235,004 B1 | 5/2001 | Steenfeldt-Jensen et al. |
| 6,248,095 B1 | 6/2001 | Giambattista et al. |
| 6,277,099 B1 | 8/2001 | Strowe et al. |
| 6,302,855 B1 | 10/2001 | Lav et al. |
| 6,340,357 B1 | 1/2002 | Poulsen et al. |
| 6,482,185 B1 | 11/2002 | Hartmann |
| 6,540,672 B1 | 4/2003 | Simonsen et al. |
| 6,558,320 B1 | 5/2003 | Causey, III et al. |
| 6,585,698 B1 | 7/2003 | Packman et al. |
| 6,663,602 B2 | 12/2003 | Moller |
| 6,781,522 B2 | 8/2004 | Sleva et al. |
| 6,875,195 B2 | 4/2005 | Choi |
| 7,138,806 B2 | 11/2006 | Gafner et al. |
| 7,195,616 B2 | 3/2007 | Diller et al. |
| 7,704,238 B2 | 4/2010 | Diller et al. |
| 7,992,460 B2 | 8/2011 | Boehen et al. |
| 8,049,519 B2 | 11/2011 | Nielsen et al. |
| 8,197,449 B2 | 6/2012 | Nielsen et al. |
| 8,529,520 B2 | 9/2013 | Daniel |
| 8,556,865 B2 | 10/2013 | Krulevitch et al. |
| 8,672,899 B2 | 3/2014 | Diller et al. |
| 9,782,543 B2 * | 10/2017 | Groeschke ........ A61M 5/31551 |
| 2001/0013774 A1 | 8/2001 | Noltemeyer et al. |
| 2002/0013522 A1 | 1/2002 | Lav et al. |
| 2002/0020654 A1 | 2/2002 | Eilersen |
| 2002/0120235 A1 | 8/2002 | Enggaard |
| 2002/0177923 A1 | 11/2002 | Steffen |
| 2003/0006209 A1 | 1/2003 | Stefen et al. |
| 2005/0182358 A1 | 8/2005 | Veit et al. |
| 2005/0182360 A1 | 8/2005 | Yeandel et al. |
| 2007/0123829 A1 | 5/2007 | Atterbury et al. |
| 2008/0140018 A1 | 6/2008 | Enggaard |
| 2009/0318865 A1 | 12/2009 | Moller et al. |
| 2010/0106098 A1 | 4/2010 | Atterbury et al. |
| 2012/0238960 A1 | 9/2012 | Smith et al. |
| 2013/0072897 A1 | 3/2013 | Day et al. |
| 2013/0245492 A1 * | 9/2013 | Klenk ............... A61M 5/31586 600/556 |
| 2013/0310756 A1 | 11/2013 | Whalley et al. |
| 2014/0074041 A1 | 3/2014 | Pedersen et al. |
| 2014/0194829 A1 | 7/2014 | Baek et al. |
| 2014/0243750 A1 | 8/2014 | Larsen et al. |
| 2015/0018775 A1 | 1/2015 | Groeschke et al. |
| 2015/0174330 A1 | 6/2015 | Nagel et al. |
| 2015/0320934 A1 | 11/2015 | Draper et al. |
| 2015/0343152 A1 | 12/2015 | Butler et al. |
| 2016/0008552 A1 | 1/2016 | Madsen et al. |
| 2016/0136353 A1 | 5/2016 | Adams |
| 2016/0259913 A1 | 9/2016 | Yu et al. |
| 2016/0296702 A1 | 10/2016 | Rasmussen et al. |
| 2016/0378951 A1 | 12/2016 | Gofman et al. |
| 2017/0023204 A1 | 1/2017 | Takeuchi et al. |
| 2017/0128674 A1 | 5/2017 | Butler et al. |
| 2017/0189625 A1 | 7/2017 | Cirillo et al. |
| 2017/0274148 A1 | 9/2017 | Mews et al. |

FOREIGN PATENT DOCUMENTS

| | | |
|---|---|---|
| EP | 0519137 | 12/1992 |
| EP | 0581925 | 2/1994 |
| EP | 0615762 | 9/1994 |
| EP | 0778034 | 6/1997 |
| EP | 0937471 | 8/1999 |
| EP | 0937472 | 8/1999 |
| EP | 1043037 | 10/2000 |
| EP | 1074273 | 2/2001 |
| EP | 1095668 | 5/2001 |
| EP | 1240913 | 9/2002 |
| EP | 2060284 | 5/2009 |
| EP | 2468340 | 6/2012 |
| EP | 2692378 | 2/2014 |
| GB | 2309801 | 8/1997 |
| WO | 9009202 | 8/1990 |
| WO | 9619872 | 6/1996 |
| WO | 0041754 | 7/2000 |
| WO | 0077472 | 12/2000 |
| WO | 0110484 | 2/2001 |
| WO | 0156635 | 8/2001 |
| WO | 0159570 | 8/2001 |
| WO | 02064196 | 8/2002 |
| WO | 02092153 | 11/2002 |
| WO | 03009461 | 1/2003 |
| WO | 03015838 | 2/2003 |
| WO | 03005891 | 11/2003 |
| WO | 2006045525 | 5/2006 |
| WO | 2011064299 | 6/2011 |
| WO | 2012004298 | 1/2012 |

(56) References Cited

FOREIGN PATENT DOCUMENTS

| WO | 2013010893 | 1/2013 |
|---|---|---|
| WO | 2013098421 | 7/2013 |
| WO | 2014037331 | 3/2014 |
| WO | 2014128157 | 8/2014 |
| WO | 2015002806 | 1/2015 |
| WO | 2015123688 | 8/2015 |
| WO | 2016180873 | 11/2016 |
| WO | 2017021226 | 2/2017 |
| WO | 2017092960 | 6/2017 |
| WO | 2017165207 | 9/2017 |
| WO | 2018031390 | 2/2018 |
| WO | 2018111708 | 6/2018 |
| WO | 2018111709 | 6/2018 |

OTHER PUBLICATIONS

Soft Pot potentiometers https://media.digikey.com/pdf/Data%20Sheets/Spectra%20Symbol/SP%20Series%20SoftPot.pdf.
Hoffman-Krippner potentiometers http://www.hoffmann-krippner.com/potentiometers-sensofoil.html.
State Electronics potentiometers https://www.potentiometers.com.
International Search Report pertaining to International Application No. PCT/US2017/045419; dated Oct. 24, 2017.
Written Opinion of the International Searching Authority pertaining to International Application No. PCT/US2017/045419; dated Oct. 24, 2017.

* cited by examiner

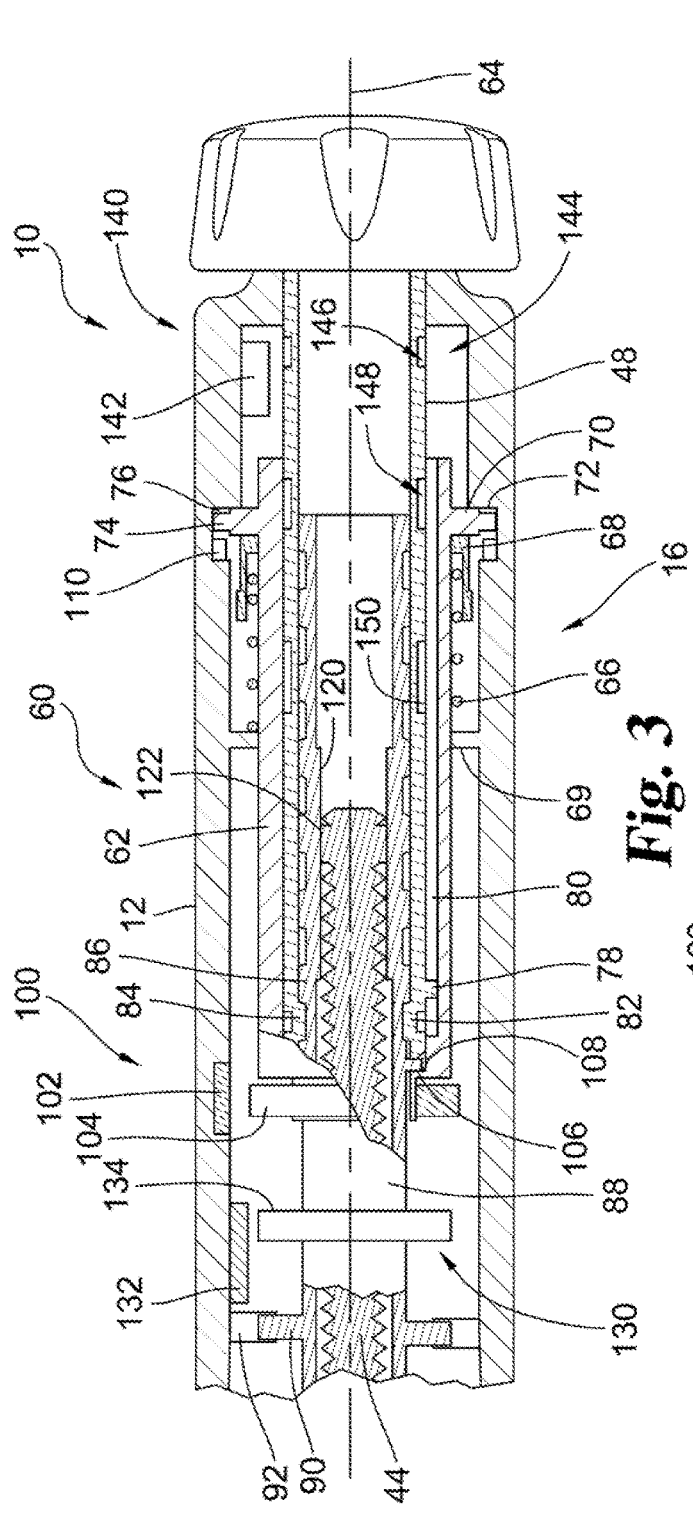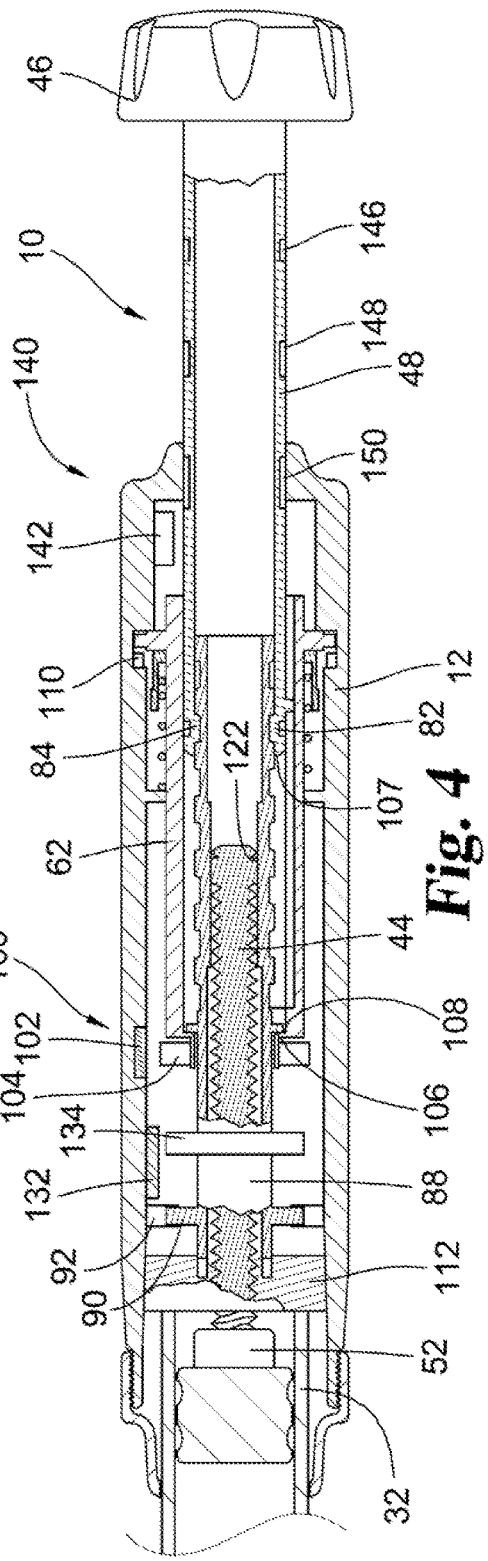

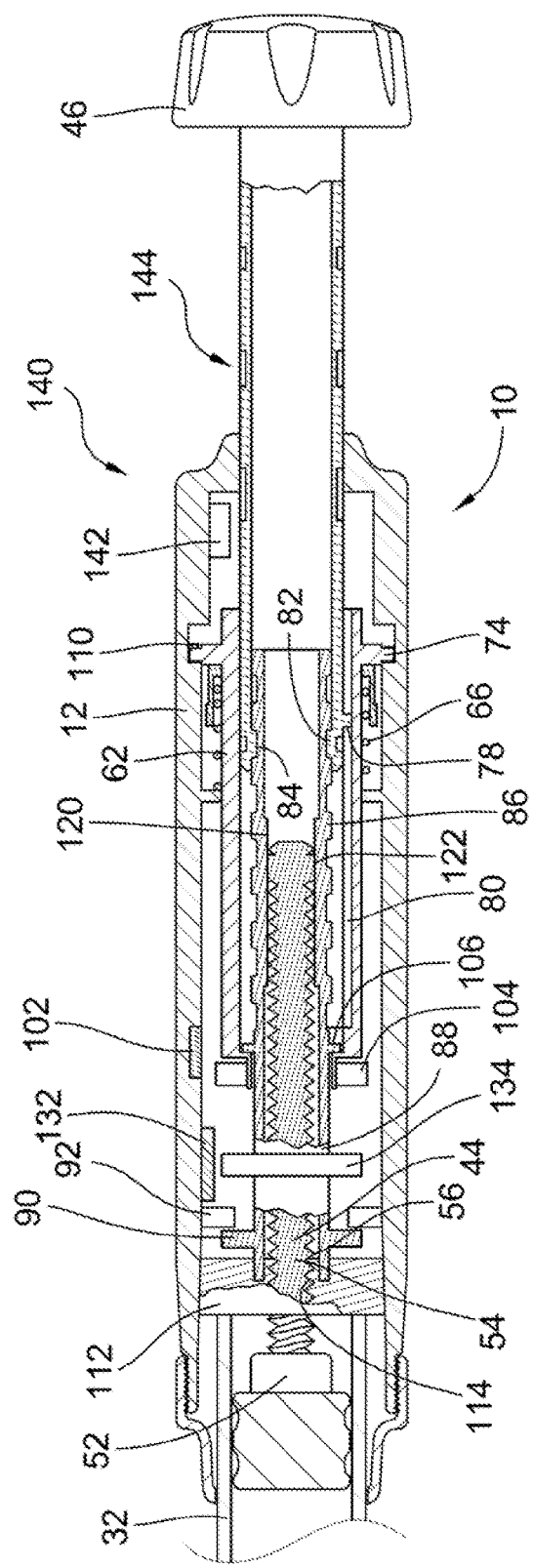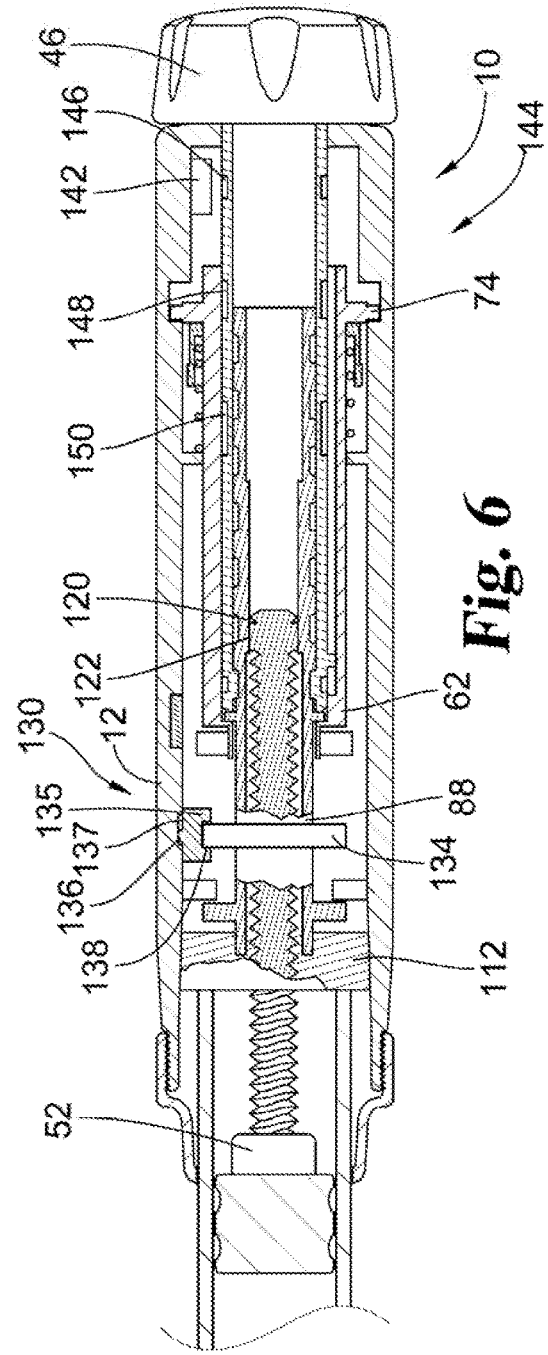

DOSE SENSING MECHANISM IN A MEDICATION DELIVERY DEVICE

BACKGROUND

The disclosure pertains to medication delivery devices, and in particular to a sensing system and methods useful with a medication delivery device to determine both the dose set and the dose delivered by operation of the medication delivery device.

A variety of medication delivery devices, including for example pen injectors, infusion pumps and syringes, are commonly used for periodic administration of medications. It is important that the proper amount of medication be supplied at these times as the health of the patient is at stake. In many instances, failure to accurately deliver the appropriate amount of medication may have serious implications for the patient.

The administration of a proper amount of medication requires that the actual dosing by the medication delivery device be accurate. The term "dosing" as used herein refers to the two key phases of administering a dose, namely, setting the dose amount and delivering the amount of the set dose. Assuring that an accurate dose is administered requires that the medication delivery device perform properly during both of these key phases of dosing.

Medication delivery devices generally utilize mechanical systems in which various members rotate or translate relative to one another. In most instances, these relative movements between members are proportional to the dose amount set and/or delivered by operation of the device. Accordingly, the art has endeavored to provide reliable systems that accurately measure the relative movement of members of a medication delivery device in order to assess the dose set and/or delivered. Such systems may include a sensor which is secured to a first member of the medication delivery device and detects the relative movement of a sensed component secured to a second member of the device. The prior art has described a variety of sensing systems, including optical, tactile, electrical and magnetic systems.

BRIEF SUMMARY

In one form thereof, the disclosure provides a medication delivery device comprising a housing; a dose dial movable in a spiral manner relative to the housing during dose setting from a start setting axial position to an end setting axial position in proportion to the amount of a dose set by operation of the medication delivery device, the dose dial also being translatable, without rotation, from a start delivery axial position to an end delivery axial position in proportion to the amount of a dose delivered by operation of the medication delivery device; a barrel rotationally coupled with the dose dial and rotatable relative to the housing during dose setting in proportion to the amount of a dose set by operation of the medication delivery device, the barrel being rotatable relative to the housing from a start setting angular position to an end setting angular position during dose setting; a drive sleeve rotatable relative to the housing during dose delivery in proportion to the amount of a dose delivered by operation of the medication delivery device, the drive sleeve being rotatable relative to the housing from a start delivery angular position to an end delivery angular position during dose delivery; an axial sensor system comprising at least one sensing component coupled with one of the housing and the barrel and at least one sensing component coupled with the dose dial, the sensing components of the axial sensor system being cooperatively configured to detect the start setting axial position and the end setting axial position and to provide start and end setting axial outputs representative of the start and end setting axial positions, respectively, the sensing components of the axial sensor system further being cooperatively configured to detect the start delivery axial position and the end delivery axial position and to provide start and end delivery axial outputs representative of the start and end delivery axial positions, respectively; a barrel sensor system comprising a sensing component rotationally coupled with the housing and a sensing component rotationally coupled with the barrel, the sensing components of the barrel sensor system being cooperatively configured to detect the start setting angular position and the end setting angular position and to provide start and end setting angular outputs representative of the start and end setting angular positions, respectively; a drive sleeve sensor system comprising a sensing component rotationally coupled with the housing and a sensing component rotationally coupled with the drive sleeve, the sensing components of the drive sleeve sensor system being cooperatively configured to detect the start delivery angular position and the end delivery angular position and to provide start and end delivery angular outputs representative of the start and end delivery angular positions, respectively; and a controller configured to determine, from the start setting axial output, the end setting axial output, the start setting angular output, and the end setting angular output, the amount of dose set by the dose dial moving from the start setting axial position to the end setting axial position, said controller also configured to determine, from the start delivery axial output, the end delivery axial output, the start delivery angular output, and the end delivery angular output, the amount of dose delivered by the dose dial moving from the start delivery axial position to the end delivery axial position.

In another form thereof, the disclosure provides a method of determining the amount of a dose set and the amount of a dose delivered by operation of a medication delivery device, the device having a housing, a dose dial movable in a spiral manner relative to the housing during dose setting from a start setting axial position to an end setting axial position, the dose dial further being translatable, without rotation, from a start delivery axial position to an end delivery axial position, a barrel rotationally coupled with the dose dial and thereby rotating with the dose dial during dose setting, the barrel being rotatable relative to the housing during dose setting from a start setting angular position to an end setting angular position, and a drive sleeve rotatable relative to the housing during dose delivery from a start delivery angular position to an end delivery angular position, the method comprising setting a dose by moving the dose dial from the start setting axial position to the end setting axial position, thereby also moving the barrel from the start setting angular position to the end setting angular position; detecting the start and end setting axial positions of the dose dial during dose setting; detecting the start and end setting angular positions of the barrel during dose setting; determining the amount of the dose setting using the start and end setting axial positions of the dose dial and the start and end setting angular positions of the barrel; delivering a dose by moving the dose dial from the start delivery axial position to the end delivery axial position, thereby also moving the drive sleeve from the start delivery angular position to the end delivery angular position; detecting the start and end delivery axial positions of the dose dial during dose delivery; detecting the start and end delivery angular positions of the drive sleeve during dose delivery; and determining the amount of the dose delivery using the start and end delivery axial positions of the dose dial and the start and end delivery angular positions of the drive sleeve.

One advantage of the disclosure is that a sensing system may be provided that provides an accurate and reliable assessment of the amount of medication that has been set and delivered by a medication delivery device.

Another advantage of the disclosure is that a sensing system may be provided that is compact and readily adapted to a variety of medication delivery devices.

Further objects, features and embodiments of the disclosure will become apparent from the detailed description and drawings provided herewith.

BRIEF DESCRIPTION OF THE DRAWINGS

The above-mentioned and other advantages and objects of this invention, and the manner of attaining them, will become more apparent, and the invention itself will be better understood, by reference to the following description of embodiments of the invention taken in conjunction with the accompanying drawings, wherein:

FIG. 3 is a partial cross-sectional view of a medication delivery device equipped with a sensing system shown in the zero dose setting position and arranged for setting a dose.

FIG. 4 is a partial cross-sectional view of the medication delivery device of FIG. 3 shown in the dose setting arrangement after setting a dose.

FIG. 5 is a partial cross-sectional view of the medication delivery device of FIG. 3 shown in the dose delivery arrangement after a state change and prior to delivering a dose.

FIG. 6 is a partial cross-sectional view of the medication delivery device of FIG. 3 shown in the dose delivery arrangement after delivering a dose.

Figure 1:
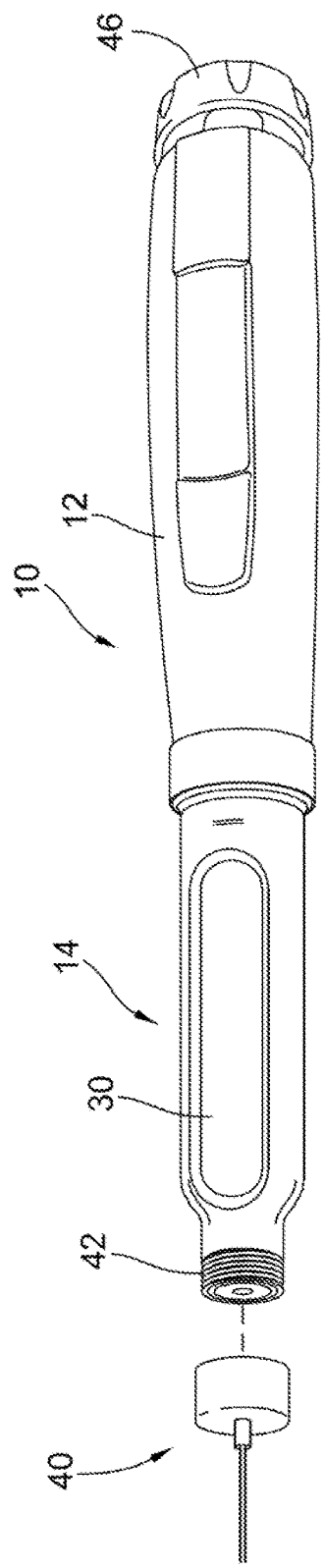
FIG. 1 is a perspective view of components of a medication delivery device including a sensing system.

Corresponding reference characters indicate corresponding parts throughout the several views. Although the drawings represent an embodiment of the present invention, the drawings are not necessarily to scale, and certain features may be exaggerated or omitted in some of the drawings in order to better illustrate and explain the present invention.

DETAILED DESCRIPTION

For the purpose of promoting an understanding of the principles of the disclosure, references are made herein to an example illustrated in the drawings, and specific language is used to describe the same. It will nevertheless be understood that no limitation of the scope of the invention is thereby intended. Any alterations and further modifications in the described embodiments, and any further applications of the concepts disclosed herein, are contemplated as would normally occur to one skilled in the relevant art. Examples of these concepts are shown in detail, but it will be apparent that some features and details have been omitted for the sake of clarity.

The disclosure relates generally to sensing systems for determining both the amount of a dose set and the amount of a dose delivered by a medication delivery device. The amounts can be determined based on the sensing of relative rotational and axial movements between members of the medication delivery device, where the sensed movements are correlated to the amount of the dose set and/or the dose delivered. The medication delivery device may be any device which is used to set and to deliver a dose of a medication, such as a pen injector or infusion device or otherwise shaped injection device. The medication may be any of a type that may be delivered by such a medication delivery device.

As used herein, the term "coupled" encompasses any manner by which a first item is caused to move in unison with or in proportion to a second item as the second item moves. Items are rotationally coupled if they are caused to rotate together. Coupling systems may include, for example, connections provided through splines, gears or frictional engagement between the members, or similar connections provided by other components which indirectly couple the members. Where applicable, an item may be coupled to another item by being directly positioned on, received within, attached to, or integral with the other item, or otherwise secured thereto.

The term "fixed" is used to denote that the indicated movement either can or cannot occur. For example, a first member is "fixed against rotation" relative to a second member if the first member is not able to rotate relative to the second member.

The overall sensing system may include at least one of dial, barrel, and drive sleeve sensor systems. In one example, each of the sensor systems includes at least a pair of sensing components. One sensing component is a sensor, and the other is referred to herein as a target. The term "sensor" refers to any component which is able to detect the relative angular or axial position of the target, as the case may be. A "target" is any component which moves relative to the associated sensor and for which the sensor is able to detect the angular or axial position of the target relative to the sensor. Thus, the sensor is able to detect the position of the target and to provide outputs representative of the relative positions of the target and the sensor, and thus of the relative positions of the members with which the sensor and target are associated.

A sensor typically detects a characteristic of a sensed parameter which varies in relationship to the position of the target within a sensed area. The target extends into or otherwise influences the sensed area in a manner that directly or indirectly affects the characteristic of the sensed parameter. The relative positions of the sensor and the target affect the characteristics of the sensed parameter, allowing the controller of the sensor system to determine different sensed positions of the target. The disclosure is useful with any of a variety of sensing technologies which operate based on any principle by which the positions of two relatively positioned members can be detected. Such technologies may include, for example, technologies based on tactile, optical or electrical measurements.

Such technologies may include the measurement of a sensed parameter associated with a field, such as a magnetic field, which is imposed upon the sensed area and which is altered based upon the position of a target within the field. The alterations of the field change the characteristic of the sensed parameter in relation to the position of the target in the sensed area. In such an embodiment, for example, the sensed parameter may be a capacitance, conductance, resistance, impedance or voltage. For example, a suitable sensing technology uses a magnetic sensor. As a more specific example, a magneto-resistive type sensor detects the distortion of an applied magnetic field which results in a characteristic change in the resistance of an element of the sensor component. Similarly, Hall Effect sensors detect changes in voltage resulting from distortions in an applied magnetic field.

As another example, a magnetic sensor may operate as an Anisotropic Magneto-Resistive (AMR) sensor or as a Giant Magneto-Resistive (GMR) sensor. An AMR uses magnets as the targets, while a GMR uses a passive structure as the target. A particular example of a GMR sensing system is disclosed, for example, in US Patent Application Ser. No. 62/324,492, filed on Apr. 19, 2016, which is hereby incorporated by reference in its entirety.

The sensor systems detect relative positions of the sensor components, and therefore of the associated members of the medication delivery device. The sensor systems produce outputs representative of the positions. In general, each system is operable to detect the position of the target relative to the sensor and to generate an output correlated thereto. A controller is operably connected to each sensor to receive the outputs. The controller is configured to determine from the outputs the amount of dose set and the amount of dose delivered by operation of the medication delivery device.

For purposes of further illustration, the configuration and operation of the disclosure is described in relation to a medication delivery device in the form of a pen injector, such as a pen injector used for the delivery of insulin for the treatment of diabetes. During dose setting and during dose delivery it is common that various members of such devices rotate and/or move axially relative to one another. These members may vary depending on the design of the medication delivery device, and may include, for example, a housing, dose knob, dose dial, drive sleeve, dosing nut and/or piston rod. It will be appreciated, however, that no limitation of the scope of the invention is intended merely by the description within the following example.

Figure 2:
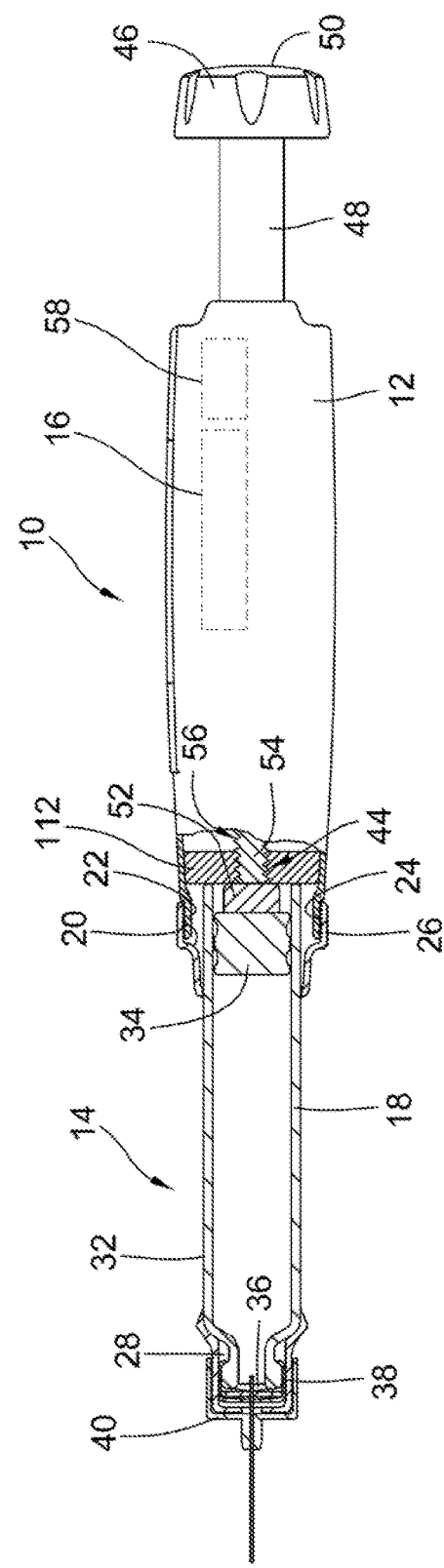
FIG. 2 is a side plan view, partially in cross section, of the medication delivery device of FIG. 1.

Referring to FIGS. 1-2, there is shown an example of a medication delivery device incorporating the sensing system. The device comprises a pen-shaped medication delivery device 10 which is manually handled by a user to selectively set a dose and then to deliver a dose. Delivery devices of this general type are well known, and the description herein of device 10 is merely illustrative. Medication delivery device 10 includes a housing 12 and a cartridge retainer 14. Housing 12 holds a mechanical drive mechanism, shown schematically at 16 (FIG. 2) and described hereafter, which is operated to set and deliver a dose of medication. Cartridge retainer 14 holds a cartridge 18 filled with medication to be delivered by the device. Cartridge retainer 14 is detachably mountable to housing 12 via external threading 20 on a protruding collar portion 22 of housing 12 which mates with internal threading 24 on a ring portion 26 at the proximal end of cartridge retainer 14. Suitable detachable mounting elements other than threadings 20 and 24, such as a bayonet fitting, are known in the art and may instead be employed. As used in the specification, the terms "proximal" and "distal" should be understood as being in the terms of an operator or user of the device delivering the medication to a patient or self. Hence the term "distal" means the portion of the delivery device that is closest to the patient's injection site (or "the injection end"), and the term "proximal" means the portion of the delivery device that is farthest from the patient's injection site (or "the operator end"), typically opposite the injection end.

Cartridge retainer 14 includes an internal hollow 28 suited to removably receive cartridge 18, thereby allowing a cartridge to be inserted therein, and then removed therefrom when depleted and replaced with a fresh cartridge of similar design. Openings 30 in cartridge retainer 14 allow visibility of the cartridge contents.

Medication cartridge 18 is of conventional design, including a body 32 having an interior reservoir filled with medication which is sealed at one end by a slidable plunger or piston 34 and sealed at the other end by a septum 36 held by a crimp ring 38.

A needle assembly 40 is detachably mountable to an externally threaded distal end 42 of cartridge retainer 14 at the injection end of the delivery device and pierces the septum 36 when so mounted. The pierced septum through which the needle extends serves as an outlet during dispensing of the medication within the reservoir of body 32, which medication is delivered through the needle assembly 40 by operation of medication delivery device 10. The cartridge 18 can hold multiple doses of medication, or even a single dose, depending on the purpose of device 10.

Medication delivery device 10 is shown in FIG. 1 in its "zero position" at which the device has not been set for delivery of any dose. In FIG. 2, device 10 is arranged after being manipulated to set a dose for delivery.

Medication delivery device 10 is typical of many such devices in including a manually-powered dose delivery mechanism that controls forward advancement of a drive member, generally designated at 44. Drive member 44 advances within the cartridge body 32 to directly engage and advance plunger 34. The dose delivery mechanism includes a dose knob 46 connected via dose dial 48 to the mechanical drive mechanism 16 within housing 12. When dose knob 46 is turned by a user to set a dose for delivery, dose knob 46 and dose dial 48 screw out together from housing 12. When a user applies a plunging force on the proximal end 50 of dose knob 46 or at the operator end of the delivery device, the resulting forward motion of dose knob 46 and dose dial 48 into housing 12, which motion is strictly translational and is not rotational due to the configuration of mechanical drive mechanism 16, is converted by the mechanical drive mechanism 16 into a smaller motion of drive member 44 forward from housing 12 into the interior of cartridge body 32. Drive member 44 is formed in two pieces including a forward end 52 that directly engages the cartridge plunger 34, and a shaft 54 connected thereto. The shaft 54 has external threads 56 and is engaged with the mechanical drive mechanism 16 to be driven axially relative to housing 12 in a screwing fashion, which fashion is due to the configuration of mechanical drive mechanism 16. Forward end 52 is provided in the form of an enlarged foot that is mounted on shaft 54. A controller 58 (FIG. 2), described later, is also provided within housing 12.

By way of example, shown in FIG. 3 is a partial, cross-sectional view of the medication delivery device 10 of FIG. 1, showing details of the mechanical drive mechanism 16 and a sensing system 60. Device 10 is similar in many respects to one taught in U.S. Pat. No. 7,195,616, the entire disclosure of which is incorporated herein by reference. During dose setting, dose dial 48 is rotated and extends proximally of the medication delivery device 10 due to a threaded connection of dose dial 48 with a drive sleeve 88. During this dose dial motion, drive sleeve 88 is rotationally fixed relative to housing 12 by splines 90 being received within complementary splines 92 of housing 12. In the course of dose setting, dose dial 48 in a dose configuration moves relative to the housing in a spiral manner from a "start" setting axial position to an "end" setting axial position. The dose dial 48 thereby moves an axial amount relative to the housing in proportion to the amount of dose set by operation of the medication delivery device 10. The axial movement of dose dial 48 is also in proportion to the rotation of the dose dial relative to the housing due to the "lead" of the spiral movement. For example, if the lead is 1 cm, then dose dial 48 will travel axially 1 cm for each complete revolution it is rotated Sensing system 60 uses rotation of a barrel 62 relative to housing 12 in determining the amount of a set dose. As indicated, dose dial 48 moves in a spiral manner about axis 64 (FIG. 3) relative to housing 12 in order to set a dose. Barrel 62 is rotationally coupled with dose dial 48 during dose setting and therefore rotates relative to the housing during dose setting in proportion to the amount of dose set by operation of the medication delivery device. In the course of dose setting, the barrel moves from a "start" setting angular position to an "end" setting angular position relative to the housing. The axial movement of dose dial 48 correlates to the number of rotations of barrel 62 relative to housing 12 as the dose dial moves from the start setting axial position to the end setting axial position during dose setting.

Sensing system 60 uses rotation of drive sleeve 88 relative to housing 12 in determining the amount of a delivered dose. In the delivery configuration, dose dial 48 moves axially, i.e., translates, relative to both housing 48 and barrel 62 during dose delivery. Axial movement of dose dial 48 causes drive sleeve 88 to rotate relative to housing 12 in proportion to the amount of dose delivered by operation of the medication delivery device. In the course of dose delivery, drive sleeve 88 moves from a "start" delivery angular position to an "end" delivery angular position relative to housing 12. In normal operation, the start angular position of drive sleeve 88 for dose delivery is the same as the start angular position of barrel 62 prior to dose setting.

During dose delivery, dose dial 48 translates distally, without rotation. In the course of dose delivery, the dose dial moves from a "start" delivery axial position to an "end" delivery axial position relative to housing 12. This translational distal movement of dose dial 48 results in, and is proportional to, the amount of rotation of drive sleeve 88 relative to housing 12 during dose delivery. The axial movement of dose dial 48 therefore correlates to the number of rotations of the drive sleeve relative to the housing as the dose dial moves from the start delivery axial position to the end delivery axial position during dose delivery.

Barrel and drive sleeve sensor systems detect the absolute positions within a given revolution of the barrel and drive sleeve relative to the housing. However, during dose setting and delivery, the barrel and drive sleeve may be rotated more or less than one revolution relative to the housing. For example, an absolute angular change of 120° of the barrel or drive sleeve relative to the housing may be the result of a rotation of 480°. The axial displacement of dose dial 48 is used to generally determine the actual rotation of the barrel and drive sleeve. For example, 1 cm of travel of the dose dial 48 may correlate to one complete revolution of the barrel or drive sleeve, in which case an axial displacement of 1.33 cm would indicate a rotation of 480°, rather than 120° or 840°. The axial positions of dose dial 48 are thereby combinable with the angular positions of barrel 62 and drive sleeve 88 relative to housing 12 to determine the "actual" amount of rotation occurring during dose setting and delivery, respectively. The axial positions of dose dial 48 are thus used to indicate the number of full revolutions of the barrel and drive sleeve relative to the housing to provide a possible adjustment to the absolute angular positions in order to determine the amount of a set or delivered dose.

Barrel 62 is received within housing 12 and is rotatable relative to the housing about axis 64. Barrel 62 is biased in the proximal direction (to the right in FIG. 3) by a spring 66 and a clicker 68, with spring 66 acting at its distal end against a shoulder 69 of housing 12. Barrel 62 includes a flange 70 which rests against a shoulder 72 of housing 12 when the barrel is in the proximal position. In this position, circumferentially-spaced teeth 74 on barrel 62 are received and move freely within an internal circumferential groove 76 of housing 12 during relative rotation of the barrel and the housing.

Dose dial 48 is received within barrel 62. A key 78 on dose dial 48 is received within longitudinal keyway 80 in barrel 62. This allows the dose dial 48 to move axially relative to the barrel 62, but prevents relative rotation between the two members. Dose dial 48 includes tabs 82 and 84 which are engaged within external threads 86 of drive sleeve 88 such that these parts are threadedly connected for spiraling motion therebetween. Drive sleeve 88 is rotatably fixed with housing 12 during dose setting by complementary splines 90 and 92. Rotation of dose dial 48 relative to drive sleeve 88 therefore causes the dial to spiral proximally and thereby move axially relative to housing 12 as tabs 82 and 84 travel along threads 86.

The setting of a dose for medication delivery device 10 occurs as follows. Barrel 62 is initially in the proximal position relative to the housing 12 (FIG. 3) and rotatable relative to housing 12 with barrel teeth 74 spinning freely within circumferential groove 76. During dose setting, dose dial 48 is rotated and spirals up external threads 86 of drive sleeve 88. The keyed connection of barrel 62 and dose dial 48 causes barrel 62 to rotate in unison with dose dial 48. However, barrel 62 at the same time is prevented from moving proximally relative to the housing in view of flange 70 being received against shoulder 72. There is therefore relative rotational movement, but no relative axial movement, between barrel 62 and housing 12 during dose setting. The relative rotational movement is indicative of the amount of dose set by operation of the medication delivery device 10.

The dose is set by rotating the dose dial 48 to the desired point, as typically indicated by a physical or electronic indicator of the set dose amount. The resulting rotation of the barrel 62 has thereby been moved from the start setting angular position to the end setting angular position relative to housing 12.

Sensing system 60 in a first aspect includes a barrel sensor system 100 which is operable to detect the angular positions of barrel 62 relative to housing 12. Barrel sensor system 100 comprises a first sensing component 102 rotationally coupled with housing 12 and a second sensing component 104 rotationally coupled with barrel 62. The barrel sensor system 100 is operable to detect and provide outputs representative of the relative start and end setting angular positions of barrel 62 relative to housing 12.

After the dose has been set, the components of the mechanical drive mechanism 16 are transitioned to prepare for delivery of a dose. This transition starts with dose knob 46, and therefore dose dial 48, being manually pushed distally. During the transition from setting to delivery, the torque required to overcome the clicker 68 and spring 66 is greater than the torque generated by the threaded connection between dose dial 48 and drive sleeve 88, and the dose dial 48 does not turn during the transition. As a result, dose dial 48 advances drive sleeve 88 without the drive sleeve rotating relative to the housing. Outwardly-extending flange 106 of drive sleeve 88 rests adjacent an interior shoulder 108 of barrel 62, and therefore barrel 62 also moves distally to the position shown in FIG. 5.

This movement causes the barrel teeth 74 to engage with housing teeth 110, and further distal movement of drive sleeve 88 and barrel 62 relative to housing 12 is prevented. Barrel 62 and keyed dose dial 48 are thus fixed against rotation relative to housing 12. This transitional movement of drive sleeve 88 also disengages drive sleeve splines 90 from housing splines 92 and the drive sleeve is therefore free to rotate relative to the housing. At this point, dose dial 48 is free to move distally, but not rotationally, relative to housing 12, and drive sleeve 88 is free to rotate, but not move distally, relative to housing 12.

Further force on dose knob 46 overcomes the frictional engagement between tabs 82 and 84 and drive sleeve threads 86 as dose knob 46 is fixed against rotation relative to housing 12. Dose dial 48 advances non-rotationally and thereby causes drive sleeve 88 to rotate relative to housing 12. Rotation of drive sleeve 88 is used to move drive member 44 axially to deliver a dose, such as shown for example in U.S. Pat. No. 7,195,616, which application is hereby incorporated by reference in its entirety. With reference to FIGS. 4-5, a drive nut 112 having an internal thread 114 receives the exterior thread 56 on shaft 54 of drive member 44. When device 10 is assembled with the cartridge loaded in the retainer, the drive nut 112 is axially movable by engagement with the cartridge 18 to the shown position. The drive nut 112 is spring loaded out (not shown) when the cartridge is removed to allow the device to reset for a new cartridge. Shaft 54 is fixed from rotation relative to drive sleeve 88 by an axial ridge 120 on drive sleeve 88 being received within groove 122 on the exterior of shaft 54. Rotation of drive sleeve 88 therefore rotates shaft 54 relative to drive nut 112, which in turn advances the drive member 44 distally to deliver the set dose. Thus, during dose delivery drive sleeve 88 rotates relative to housing 12 in an amount representative of the amount of dose delivered by operation of the medication delivery device.

The dose is delivered by pressing the dose dial 48 to its end of travel relative to the housing. The drive sleeve 88 has thereby rotated from the start delivery angular position to the end delivery angular position relative to housing 12.

Sensing system 60 further includes a drive sleeve sensor system 130, in addition to or alternative to the barrel sensor system 100, which is operable to detect the angular positions of drive sleeve 88 relative to housing 12. Drive sleeve sensor system 130 comprises a first sensing component 132 rotationally coupled with housing 12 and a second sensing component 134 rotationally coupled with drive sleeve 88. The drive sleeve sensor system detects and generates outputs indicative of the relative start and end delivery angular positions of the drive sleeve relative to the housing.

Determination of the amount of the doses set and delivered by operation of the medication delivery device additionally uses information concerning the axial positions of the dose dial. The relative movements of the barrel and the drive sleeve during dose setting and delivery, respectively, are correlated to the amount of dose set and delivered. However, the absolute change in relative angular positioning alone does not always indicate the amount of dose set or delivered. For a device in which these members may rotate more than a full revolution during dose setting and delivery, "absolute" change in angular positions from start to end may not reflect that the members have moved as much as, or more than, a single revolution. The number of full revolutions made by the barrel during dose setting and by the drive sleeve during dose delivery may be determined. For example, the number of full revolutions made by the members is determined based on the axial positions of the dose dial.

One of the features of the axial sensor system is to provide outputs indicating the axial movement of the dose dial such that the number of full revolutions of the barrel and dose sleeve may be determined. In this respect, it is sufficient if the axial sensor provides outputs indicating that the dose dial is within any one range of a plurality of ranges of axial positions of the dose dial relative to the housing. Each range of axial positions corresponds to a range of a plurality of ranges of revolutions relative to the housing that the dose dial and barrel turn during dose setting, and that the drive sleeve turns during dose delivery. Thus, the end setting axial output is indicative of a range of positions corresponding to the number of rotations the barrel has rotated upon movement of the dose dial from the start setting axial position to the end setting axial position, and the end delivery axial output is indicative of a range of positions corresponding to the number of rotations the drive sleeve has rotated upon movement of the dose dial from the start delivery axial position to the end delivery axial position One of the advantages of the disclosure therefore is the ability to use a relatively simple axial sensor to detect the number of full revolutions completed by the barrel during dose setting and by the drive sleeve during dose delivery. Because the dose dial moves a significant axial distance to complete a revolution, the axial sensor system may have a lesser degree of accuracy than if it were to be used by itself to determine the dose setting/delivery. That is, an accurate determination of the rotational movement can be used with a less accurate determination of axial movement. For example, if the absolute rotational movement is determined to be 60°, then determination of the corresponding axial movement need only be accurate enough to know whether the rotational movement was less than one revolution, more than one but less than two revolutions, etc. Thus, it is sufficient accuracy for the axial sensor system if the number of complete revolutions is apparent based on a consideration of both the approximate axial displacement and the associated absolute angular displacement. This allows for the use of a simpler and less expensive axial sensor system.

In normal operation, the medication delivery device starts in a zeroed position (FIG. 3). The "zero position" is the position in which dose dial 48 is in its most distal position with a distal end 107 of dose dial 48 resting against flange 106 of drive sleeve 88. When a dose is started to be set from the zero position, this most distal position of the dose dial equates to the start setting axial position. At this time, the barrel and drive sleeve are also in the "start" setting and delivery positions, respectively. Once a dose has been set, it is possible to adjust that dose up or down prior to delivery of the dose. It is also possible to deliver a portion of a set dose and then to dial up an additional dose amount, or to dial down some of all of the remaining dose amount. In any of these instances, the dose dial is eventually returned to the zero position.

The axial sensor system is operable to detect all of the relevant axial positions of the dose dial during dose setting and dose delivery. As already described, the axial sensor system includes sensing components which are used to detect starting and ending positions during both setting and delivery. These same components may also be used to detect when the dose dial is in the zero position relative to the housing.

The axial sensor system may alternatively or additionally include separate sensing components, e.g., dedicated components, which specifically confirm when the dose dial is in the zero position. This may comprise, for example, a sensing component coupled with dose dial 48 and a sensing component coupled with housing 12, barrel 62 or drive sleeve 88. This aspect of the sensing system may detect the zero position by a simple contact switch or similar item which is operable to detect when dose dial 48 has bottomed out against drive sleeve 88. In this approach, the axial sensor system may involve components which are specifically dedicated to detecting the zero position of the dose dial.

In comparison to other relevant positions of the dose dial, the zero position is a physical position relative to the housing and other components. Therefore, unlike the other dosing positions which may be somewhat approximated, the zero position is more specific. At the same time, the zero position is readily determined as it is marked by distinct physical relationships that are easily identified. As is well known in the art, for example, the zero position could be detected using sensing components which make contact when the distal end 107 of dose dial 48 bottoms out against flange 106, or when dose knob 46 rests against housing 12.

Axial sensor system 140 (FIG. 3), in addition to or alternative to barrel sensor system 100 and/or drive sleeve sensor system 130, also detects other positions of dose dial 48 in relation to dose setting and dose delivery. Once the amount of a dose has been set, dose dial 48 will have been moved proximally from a start setting axial position, such as shown in FIG. 3, to an end setting axial position, such as shown in FIG. 4. Axial sensor system 140 is operable to detect the end setting axial position. In this aspect, the axial sensor system may comprise a sensing component 142 coupled with housing 12 or barrel 62, and a sensing component 144 coupled with dose dial 48. These sensing components similarly are operable to detect the start delivery axial position, including the zero position.

The axial sensor can detect a considerable extent of relative axial movement in view of the travel of the dose dial during dose setting and delivery. This may be readily accomplished by selection of appropriate sensing components. For example, either of the sensing components may be a single sensing element which is capable of detecting, and/or being detected, over the full length of relative axial travel. For example, the sensor system may include a target which extends along the dose dial 48 for enough of a distance that its position may be determined by a single sensor on the housing for any useful position relative to the sensor, e.g., it may form a continuous physical element along the dose dial. Alternatively, the sensor system may employ a sensor having a broad sensing range that extends axially for the full travel of the dose dial. In either instance, the advantage remains that the axial positions need only be determined with sufficient particularity that the number of rotations of the dose dial can be determined.

In another approach, one or both of the sensing components may comprise a plurality of discrete sensing elements appropriately spaced along the associated member(s) of the medication delivery device. For example, as schematically represented in the drawings, one embodiment of the axial sensor system may comprise a series of targets 146, 148, 150 positioned along the dose dial 48, axially disposed relative to one another, with a single sensor coupled with the housing. The targets 146, 148, 150 are then configured such that their relative positions can be separately identified for the movement of the dose dial, such as by varied sizes or spacing. Alternatively, the axial sensing system could have multiple sensors coupled with the housing, barrel or dose dial, which detect the position of one or more targets coupled with the other relatively-moving member. The design of the axial sensing system is facilitated by the axial sensor system not being required to provide a high degree of accuracy as to the axial positions of the dose dial.

Dose dial 48 also moves axially relative to barrel 62, as well as the housing, during dose setting. Therefore, in an alternate embodiment the axial sensor system may include one sensing component coupled with the dose dial and the other sensing component coupled with the barrel. A potential advantage of this approach is that the dose dial does not move axially relative to the barrel during the transition between dose setting and dose delivery. Using the dose dial and the barrel to measure relative axial movement therefore would normally exclude the measurement of any relative axial movement other than movement during dose setting and dose delivery.

Once the dose has been set, the medication delivery device transitions to a condition in which a dose may be delivered. In some embodiments, this may not involve any relative movement of the members associated with dose setting or delivery. However, in the disclosed embodiment, this transition involves a slight distal movement of the dose dial relative to the housing. As the dose dial is initially pushed distally after dose setting, the tabs 82 and 84 remain frictionally engaged with the external threads 86 of the drive sleeve. The dose dial, barrel and drive sleeve all translate together without rotation relative to the housing 12. Once the barrel teeth 74 are received by housing teeth 110, further distal movement of these members is ended.

During this initial movement, there is no rotation of the drive sleeve relative to the housing, and this axial movement of the dose dial therefore is unrelated to the amount of dose delivered by the medication delivery device. Thus, the relevant "start" axial position of dose dial 48 with respect to dose delivery may be considered to be either the end setting axial position prior to the transitional movement, or the new axial position after the transitional movement.

Thus, it may occur that a medication delivery device may include members which at times have movement relative to one another when a dose is not being set or delivered. In such a situation, the sensing system may be configured to account for this by measuring only that portion of the relative movement that is correlated to the amount of dose set or delivered. This would occur in the disclosed embodiment, for example, if the start delivery axial position is determined by the position after the transitional displacement of the members has taken place. Alternatively, the start position could be determined by the end setting axial position reduced by the known amount of transitional movement, i.e., the movement that is not correlated to dose delivery. This may also be accommodated, for example, by mathematical or other methods of compensation programmed into a controller. In any event, the principle remains the same that the sensing system determines the amount of dose setting or delivery based upon the positions of the members that are indicative of the dosing.

Once the transition is completed, any further distal movement of dose dial 48 results in rotation of drive sleeve 88 relative to housing 12 and causes medication to be delivered. During dose delivery, the dose dial moves from a start delivery axial position, such as shown in FIG. 5, to an end delivery axial position, such as shown in FIG. 6, when the dose has been delivered. The axial displacement, in combination with the absolute angular change between the drive sleeve and the housing, are indicative of the amount of dose delivered by operation of the medication delivery device. Once the dose has been delivered, the user releases pressure on the dose dial. In response, spring 66 urges clicker 68 to the proximal position, carrying barrel 62 and other components back to the position shown in FIG. 3.

The medication delivery device may alternately use as the start delivery axial position either the end setting axial position, or a newly determined start delivery axial position, which may be either before or after any transitional movement in preparing for dose delivery. At some point, the user releases the pressure sufficiently that the barrel and drive sleeve are moved proximally and the drive sleeve is fixed against rotation relative to the housing. At this time, the medication delivery device detects an end delivery axial position for the dose dial, and an end delivery angular position for the drive sleeve, and corresponding outputs are generated.

In the zero position, barrel 62 and drive sleeve 88 may be considered to be at the start set position for the barrel and the start delivery position for the drive sleeve. In the normal operation of the medication delivery device, the barrel and drive sleeve are in the same relative rotational positions after dose delivery as when in the "zero position" prior to setting a dose. However, their position relative to the housing may differ. For example, if dose dial 48 is rotated 120° to set a dose and that dose is fully delivered, then dose dial 48 will again be in the bottomed-out, zero position, but the barrel and drive sleeve will have both rotated 120° in the same direction from their prior zero position.

Once a dose has been set, the barrel will have moved a rotational amount from its start position. Since the drive sleeve is not intended to rotate during dose setting, then the barrel should have moved the same rotational amount relative to the drive sleeve as it has relative to the housing. The barrel sleeve and drive sleeve sensors can be used to confirm this. Conversely, during dose delivery the barrel is fixed rotationally with the housing and the drive sleeve rotates relative to both the barrel and the housing. If the drive sleeve rotates the same amount during dose delivery as the barrel rotated during dose setting, then a complete delivery of the set dose is generally indicated. The controller of the device can recognize a delivery versus a setting of a dose by monitoring a sensor of the device, such as an additional not shown electrical switch activated by axial motion of a component that occurs during a delivery. Such an axially moving component may be the barrel, or the sensing component 135, which serves as a slider as described below. In one respect then, the barrel sensor system and the drive sleeve sensor system may be used at the end of dose delivery to check whether the barrel and drive sleeve have again aligned at a zero position relative to one another. If the dose dial is in the zero dose position and the barrel and drive sleeve are back to their original pre-setting relative positions, then the complete amount of set dose has been delivered. Once this has been confirmed, then the amount of dose delivered may be determined and the information recorded and provided to the user. One way to so determine the delivered dose is for the controller to hold the set dose in temporary memory, and, when the zero position has been reached and the barrel and drive sleeve are aligned, to formally record in dose memory, or transmit to an external device, such set dose quantity as the delivered dose. If after dose delivery the dose dial is in the zero dose position but the relative rotational positions of the barrel and drive sleeve are not aligned as they were before the dose was set, then an instruction and/or error message may be provided to the user. For example, the user may be instructed to take steps to reset the medication delivery device in order to place the barrel and drive sleeve into a zero position. Steps may also be taken to determine the amount of dose actually delivered rather than the amount set to be delivered, to ensure that delivery information is provided accurately to the controller or an external device. For example, the current position of the drive sleeve relative to the barrel sleeve could be used to determine the amount of undelivered dose, and thus the amount of dose actually delivered could be determined and stored and/or exported.

It is possible for a user to stop the delivery of a dose before the total amount of the set dose has been delivered. Upon removing pressure against the dose knob which would cause the slider described above to return axially and deactivate the switch allowing the controller to recognize dose delivery has stopped, the medication delivery device, via its controller checking inputs from one or more sensors, may check the position of the dose dial. If the dose dial is not at the zero position, then that is an indication that the set dose has not been completely delivered. An alarm or instruction may be provided to the user to conclude the dose delivery. One option is for the user to resume dose delivery to conclusion without the user adjusting the dial. If delivery is so resumed to completion, the device would function as described above. If the device times out without further user action, then the partial dose delivered could be recorded into the device's memory. Such partial dose may be determined by the controller considering the instant sensor outputs from the barrel sensor and drive sleeve sensor to determine relative rotational positions of these sensed elements, and the instant sensor output of the dose dial sensor, which determination can be confirmed by the controller by determining the rotation of the drive sleeve during delivery as recognizable from the operation of the drive sleeve sensor during, and/or at the start and end of, dose delivery. Alternatively, the device may wait until the user either continues the dose or adjusts the dose size to determine what action to take.

Alternatively, an additional amount of dose may be dialed up. Then the medication delivery device is operable to detect the new end setting axial position of the dose dial and the new end setting angular position of the barrel, in the manner previously described, such as with confirmation that the drive sleeve has not rotated or changed its rotational position during such dial up. The original dose delivered may be added to this new dose setting to determine the total dose subsequently delivered by plunging the dial to the zero position, which total dose may be recorded or transmitted. Alternatively, the device could record the partial dose delivered as soon as the dialed dose is adjusted. In this case, the new dialed dose would be handled by the device as a separate dosing event. Still alternatively, the incremental amount of dose that was dialed up may be determined and added to the originally set dose, and the total dose subsequently delivered by plunging the dial to the zero dose position would be recognized by the controller as equal to the originally set dose plus the additional incremental dose, which total dose would be recorded or transmitted.

Conversely, the dose setting of the medication delivery device may be partially or completely dialed down. The sensing system and controller are then operable to determine the amount of dose reduction. Once the dose dial has been returned to the zero position, the total dose delivered would be recognized by the controller as equal to the originally set dose minus the dialed dose reduction, which total dose would be recorded or transmitted.

The barrel and drive sleeve sensor systems are shown somewhat diagrammatically in the drawings. As indicated, the paired components of the sensing components can be positioned to provide sensing of locations during the full range of positions which may be assumed during operation of the medication delivery device. However, in certain embodiments it is typical for a medication delivery device to have a transitional stage, as described herein, when certain components are moved axially between dose setting and dose delivery conditions. This can allow for changing the relationship between the relevant members for the two dosing steps. For example, in the described embodiment the drive sleeve is fixed rotationally with the housing during dose setting and the barrel is fixed rotationally with the housing during dose delivery. The transitional, distal movement of the drive sleeve, barrel and dose dial between dose setting and dose delivery provides one manner of changing these relationships, as above described.

This transitional movement can change the relative axial positions of the paired rotational members, and therefore of the sensing components associated with those members. This is demonstrated, for example, by the relative positions of sensing component 132 and sensing component 134 of the drive sleeve sensor system in FIGS. 4 and 5. Prior to the transitional movement (FIG. 4), the sensing component 134 is proximal of the center of sensing component 132. After the transitional movement (FIG. 5), the sensing component has moved to the center of sensing component 132. As shown in the drawings, the sensing components of the barrel and drive sleeve sensor systems may thus be positioned to have the proper alignment during dose setting and dose delivery, respectively. One or both of the sensor components may be coupled with the associated member(s) in a manner to move axially relative to that member, while being fixed to rotate with that member. This is shown in somewhat schematic form in FIG. 6. Sensing component 135 includes a key 136 which is received within a longitudinal keyway 137 in the interior surface of housing 12. Sensing component 135 further includes arms 138 which extend out on opposite sides of sensing component 134. In this manner, axial movement of the drive sleeve 88 will cause the sensing component 135 to slide axially relative to housing 12 a commensurate amount. This maintains the same alignment, without relative axial movement, between the sensing components 135 and 134. This is useful, for example, if these components comprise electrical contacts which extend from one component to the other. A sensing system of this general type is disclosed in U.S. Pat. No. 7,195,616, previously incorporated herein in its entirety.

One feature of the sensing system is that each sensor system may be dedicated to the specific measurements recited, with the elements of each system being used only for the specific purpose of that system. For example, the barrel sensor system components may only be used to measure rotational movement between the barrel and the housing during dose setting, the drive sleeve system components may only be used to measure rotational movement between the drive sleeve and the housing during dose delivery, and the axial sensor system may only be used to measure axial movement between the dose dial and the housing during dose setting and dose delivery. One result of this is that each sensor component and system may be optimized for the specifically assigned task.

A controller 58 (FIG. 2) is operably connected to each of the axial, barrel and drive sleeve sensor systems to receive the outputs. The controller may include conventional components such as a processor, power supply, memory, microcontrollers, etc. Controller 58 is shown in FIG. 2 as being secured to the housing 12 of medication delivery device 10. Alternatively, all or part of the controller may be provided separately, such as by means of a computer, smart phone or other device. Means are then provided to operably connect the controller components with the sensor at appropriate times, such as by a wired or wireless connection.

The controller is configured to receive the outputs from the sensor systems which may be used to determine the amount of dose set and the amount of dose delivered by the medication delivery device. The controller is configured to determine from the start setting axial output, the end setting axial output, the start setting angular output, and the end setting angular output the amount of dose set by the dose dial moving from the start setting axial position to the end setting axial position. The controller is also configured to determine from the start delivery axial output, the end delivery axial output, the start delivery angular output, and the end delivery angular output the amount of dose delivered by the dose dial moving from the start delivery axial position to the end delivery axial position. The controller is also operable to determine from the end setting angular output and the end delivery angular output whether the barrel and drive sleeve are rotationally aligned in the same relative position after dose delivery as before dose setting.

A method is therefore provided for determining the amount of a dose set and the amount of a dose delivered by operation of a medication delivery device. The device includes a housing, and a dose dial movable in a spiral manner relative to the housing during dose setting from a start setting axial position to an end setting axial position, and translatable, without rotation, relative to the housing during dose delivery from a start delivery axial position to an end delivery axial position. The device further includes a barrel rotationally coupled with the dose dial and thereby rotating with the dose dial during dose setting. The barrel is rotatable relative to the housing during dose setting from a start setting angular position to an end setting angular position. The device also includes a drive sleeve rotatable relative to the housing during dose delivery from a start delivery angular position to an end delivery angular position.

The method comprises setting a dose by moving the dose dial from the start setting axial position to the end setting axial position, thereby also moving the barrel from the start setting angular position to the end setting angular position. The medication delivery device is operated to detect the start and end setting axial positions of the dose dial during dose setting, and the start and end setting angular positions of the barrel during dose setting. The amount of the dose set is determined using the start and end setting axial positions of the dose dial and the start and end setting angular positions of the barrel.

The method further comprises delivering a dose by moving the dose dial from the start delivery axial position to the end delivery axial position, thereby also moving the drive sleeve from the start delivery angular position to the end delivery angular position. The method then includes detecting the start and end delivery axial positions of the dose dial during dose delivery, and detecting the start and end delivery angular positions of the drive sleeve during dose delivery. Finally, the amount of the dose delivered is determined using the start and end delivery axial positions of the dose dial and the start and end delivery angular positions of the drive sleeve.

The method may include determining prior to dose setting whether the dose dial is in a zero position relative to the housing. A signal may be provided to indicate that the dose dial is not in the zero position. Further, if it is determined that the dose dial is not in a zero position relative to the housing at the time of dose setting, then the method includes moving the dose dial into a zero position relative to the housing. The method may further include, following dose delivery, determining whether the dose dial is in a zero position relative to the housing. Upon determining that the dose dial is not in the zero position relative to the housing, a signal may be provided indicating that the dose dial is not in the zero position, and the method may also involve moving the dose dial into the zero position.

The method may further include, following dose delivery, determining from the end setting angular position of the barrel and the end delivery angular position of the drive sleeve whether the barrel and drive sleeve are rotationally aligned in the same relative position after dose delivery as before dose setting. The method further includes, upon determining that the barrel and the drive sleeve are not rotationally aligned in the same relative position after dose delivery as before dose setting, providing a signal indicating that the barrel and drive sleeve are not so aligned.

Since the sensing systems measure relative movement, the particular members with which the sensor and target are associated are completely reversible. However, the placement of the two sensor components may be dictated to some extent on other factors, such as the space that is available. Positioning of the sensor on the housing is advantageous to facilitate its connection to a power supply and with electronics used to receive, process, display and record the determined amounts of dose that are set and delivered. In a typical embodiment, the sensor is secured with an outer member such as the housing, and the target is secured with an opposed, inner member. However, it will be appreciated by those skilled in the relevant art that for any embodiment of the disclosure the placement of the sensor and the target may be reversed.

Particularly structures have been used herein, but are not to be considered limiting. It will be appreciated by those skilled in the art that medication delivery devices may be configured in varying ways for which the disclosure is applicable. In general, it is contemplated that the delivery device includes a first pair of members which rotate relative to one another in proportion to the amount of dose set, and that a second pair rotate in proportion to the amount of dose delivered. It further is contemplated that a third pair of members move axially relative to one another in relation to the relative rotation of the first and second pairs of members, and thus may be used to determine the number of revolutions occurring between the first pair of members during dose setting and the second pair of members during dose delivery. In this respect, the barrel and the housing in the described embodiment represent the first pair of members, the drive sleeve and the housing represent the second pair of members, and the dose dial and the housing represent the third pair of members.

While the invention has been illustrated and described in detail in the drawings and foregoing description, the same is to be considered as illustrative and not restrictive in character. All changes, equivalents, and modifications that come within the spirit of the inventions defined by the claims included herein are desired to be protected.

Various aspects are described in this disclosure, which include, but are not limited to, the following aspects.

1. A medication delivery device, comprising: a housing; a dose dial movable in a spiral manner relative to said housing during dose setting from a start setting axial position to an end setting axial position in proportion to the amount of a dose set by operation of the medication delivery device, said dose dial also being translatable, without rotation, from a start delivery axial position to an end delivery axial position in proportion to the amount of a dose delivered by operation of the medication delivery device; a barrel rotationally coupled with said dose dial and rotatable relative to said housing during dose setting in proportion to the amount of a dose set by operation of the medication delivery device, said barrel being rotatable relative to said housing from a start setting angular position to an end setting angular position during dose setting; a drive sleeve rotatable relative to said housing during dose delivery in proportion to the amount of a dose delivered by operation of the medication delivery device, said drive sleeve being rotatable relative to said housing from a start delivery angular position to an end delivery angular position during dose delivery; an axial sensor system comprising at least one sensing component axially coupled with one of said housing and said barrel and at least one sensing component axially coupled with said dose dial, the sensing components of said axial sensor system being cooperatively configured to detect the start setting axial position and the end setting axial position and to provide start and end setting axial outputs representative of the start and end setting axial positions, respectively, the sensing components of said axial sensor system further being cooperatively configured to detect the start delivery axial position and the end delivery axial position and to provide start and end delivery axial outputs representative of the start and end delivery axial positions, respectively; a barrel sensor system comprising a sensing component rotationally coupled with said housing and a sensing component rotationally coupled with said barrel, the sensing components of said barrel sensor system being cooperatively configured to detect the start setting angular position and the end setting angular position and to provide start and end setting angular outputs representative of the start and end setting angular positions, respectively; a drive sleeve sensor system comprising a sensing component rotationally coupled with said housing and a sensing component rotationally coupled with said drive sleeve, the sensing components of said drive sleeve sensor system being cooperatively configured to detect the start delivery angular position and the end delivery angular position and to provide start and end delivery angular outputs representative of the start and end delivery angular positions, respectively; and a controller configured to determine from the start setting axial output, the end setting axial output, the start setting angular output, and the end setting angular output the amount of dose set by said dose dial moving from the start setting axial position to the end setting axial position, said controller also configured to determine from the start delivery axial output, the end delivery axial output, the start delivery angular output, and the end delivery angular output the amount of dose delivered by said dose dial moving from the start delivery axial position to the end delivery axial position.

2. The medication delivery device of aspect 1 in which the end setting axial output is indicative of a range of positions corresponding to the number of rotations the barrel has rotated upon movement of the dose dial from the start setting axial position to the end setting axial position, and further in which the end delivery axial output is indicative of a range of positions corresponding to the number of rotations the drive sleeve has rotated upon movement of the dose dial from the start delivery axial position to the end delivery axial position.

3. The medication delivery device of any one of aspects 1-2 in which said controller is operable to determine from the start and end setting axial outputs the number of complete revolutions of said barrel relative to said housing during dose setting, and in which said controller is operable to determine from the start and end delivery axial outputs the number of complete revolutions of said drive sleeve relative to said housing during dose delivery.

4. The medication delivery device of any one of aspects 1-3 in which said controller is operable to determine from the end setting angular output and the end delivery angular output whether the barrel and drive sleeve are rotationally aligned in the same relative position after dose delivery as before dose setting.

5. The medication delivery device of any one of aspects 1-4 in which said controller is operable to determine the amount of dose set using only the start and end setting axial outputs and the start and end setting angular outputs, and in which said controller is operable to determine the amount of dose delivered using only the start and end delivery axial outputs and the start and end delivery angular outputs.

6. The medication delivery device of any one of aspects 1-5 in which one sensing component of each of said axial, barrel and drive sleeve sensor systems comprises a sensor and the other sensing component of each sensor system comprises a target, and in which each sensor is secured to said housing.

7. The medication delivery device of any one of aspects 1-6 in which the sensing components of said axial sensor system are further cooperatively configured to detect a zero position of said dose dial.

8. A method of determining the amount of a dose set and the amount of a dose delivered by operation of a medication delivery device, the device having a housing, a dose dial movable in a spiral manner relative to the housing during dose setting from a start setting axial position to an end setting axial position, the dose dial further being translatable, without rotation, relative to the housing during dose delivery from a start delivery axial position to an end delivery axial position, a barrel rotationally coupled with the dose dial and thereby rotating with the dose dial during dose setting, the barrel being rotatable relative to the housing during dose setting from a start setting angular position to an end setting angular position, and a drive sleeve rotatable relative to the housing during dose delivery from a start delivery angular position to an end delivery angular position, the method comprising: setting a dose by moving the dose dial from the start setting axial position to the end setting axial position, thereby also moving the barrel from the start setting angular position to the end setting angular position; detecting the start and end setting axial positions of the dose dial during dose setting; detecting the start and end setting angular positions of the barrel during dose setting; determining the amount of the dose setting using the start and end setting axial positions of the dose dial and the start and end setting angular positions of the barrel; delivering a dose by moving the dose dial from the start delivery axial position to the end delivery axial position, thereby also moving the drive sleeve from the start delivery angular position to the end delivery angular position; detecting the start and end delivery axial positions of the dose dial during dose delivery; detecting the start and end delivery angular positions of the drive sleeve during dose delivery; and determining the amount of the dose delivery using the start and end delivery axial positions of the dose dial and the start and end delivery angular positions of the drive sleeve.

9. The method of aspect 8 and which further includes, prior to dose setting, determining whether the dose dial is in a zero position relative to the housing.

10. The method of aspect 9 and which further includes, prior to dose setting, determining that the dose dial is not in a zero position relative to the housing and moving the dose dial into a zero position relative to the housing.

11. The method of any one of aspects 8-10 and which further includes, following dose delivery, determining whether the dose dial is in a zero position relative to the housing.

12. The method of aspect 11 and which further includes, following dose delivery, determining that the dose dial is not in the zero position relative to the housing and providing a signal indicating that the dose dial is not in the zero position.

13. The method of any one of aspects 8-12 in which said detecting the end setting axial position of the dose dial comprises determining that the end setting axial position is within a range of positions corresponding to the number of rotations the barrel rotated upon movement of the dose dial from the start setting axial position to the end setting axial position, and in which said detecting the end delivery axial position of the dose dial comprises determining that the end delivery axial position is within a range of positions corresponding to the number of rotations the drive sleeve rotated upon movement of the dose dial from the start delivery axial position to the end delivery axial position.

14. The method of any one of aspects 8-13 and which further includes, following dose delivery, determining from the end setting angular position of the barrel and the end delivery angular position of the drive sleeve whether the barrel and drive sleeve are rotationally aligned in the same relative position after dose delivery as before dose setting.

15. The method of aspect 14 and which further includes determining that the barrel and the drive sleeve are not rotationally aligned in the same relative position after dose delivery as before dose setting, and providing a signal indicating that the barrel and drive sleeve are not so aligned.

16. A medication delivery device, comprising: a housing; a dose dial having a dose configuration and a delivery configuration, in the dose configuration, the dose dial is movable in a spiral manner relative to said housing between axial positions, and in the delivery configuration, the dose dial is translatable between delivery axial positions; a barrel coupled around the dose dial in a manner for rotation with the dose dial in the dose configuration and rotationally fixed for translatable contact with the dose dial in the delivery configuration; a drive sleeve coupled within the dose dial in a manner for rotation with dose dial in the delivery configuration from a start delivery angular position to an end delivery angular position; an axial sensor system comprising a first sensing component axially coupled with one of the housing and the barrel and a second sensing component axially coupled with the dose dial, the first and second sensing components of the axial sensor system being cooperatively configured to detect and provide outputs indicative of the axial positions of the dose dial in the dose configuration and outputs indicative of the delivery axial positions of the dose dial in the delivery configuration; a drive sleeve sensor system comprising a first sensing component coupled with the housing and a second sensing component coupled with the drive sleeve, the first and second sensing components of the drive sleeve sensor system being cooperatively configured to detect and provide outputs indicative of the start delivery angular position and the end delivery angular position; and a controller operably connected to the axial and drive sleeve sensor systems, and, from the outputs received, configured to determine the amount of dose delivered by the dose dial when in the delivery configuration.

17. The medication delivery device of aspect 16, further comprising a barrel sensor system including a first sensing component coupled with the housing and a second sensing component coupled with the barrel, the first and second sensing components of the barrel sensor system being cooperatively configured to detect and provide outputs indicative of a start setting angular position and an end setting angular position when the dose dial is in the dose configuration, and the controller operably connected to the barrel sensor system.

18. The medication delivery device of aspect 17, wherein the first and second sensing components of the drive sleeve sensor system is disposed distal to the first and second sensing components of the barrel sensor system.

19. The medication delivery device of any one of aspects 16-18, wherein the second sensing component of the axial sensor system comprises a plurality of targets positioned axially disposed relative to one another along the dose dial.

20. The medication delivery device of any one of aspects 17-19, wherein the controller is operable to: determine from the outputs indicative of the start setting angular position and the end setting angular position a total amount of angular rotation of the barrel relative to the housing when the dose dial in the dose configuration; determine from the outputs indicative of the start delivery angular position and the end delivery angular position a total amount of angular rotation of the drive sleeve relative to the housing when the dose dial is in the delivery configuration; determine the amount of dose set using the outputs indicative of the axial positions of the dose dial in the dose configuration and the total amount of angular rotation of the barrel; and determine the amount of dose delivered using the outputs indicative of the delivery axial positions of the dose dial in the delivery configuration and the total amount of angular rotation of the drive sleeve.

| Table of Drawing Numbers | |
|---|---|
| 10 | device |
| 12 | housing |
| 14 | cartridge retainer |
| 16 | mechanical drive mechanism |
| 18 | cartridge |
| 20 | external threading |
| 22 | collar portion of 12 |
| 24 | internal threading on ring portion 26 |
| 26 | ring portion on 14 |
| 28 | hollow |
| 30 | openings |
| 32 | cartridge body |
| 34 | plunger |
| 36 | septum |
| 38 | crimp ring |
| 40 | needle assembly |
| 42 | externally threaded distal end |
| 44 | drive member |
| 46 | dose knob |
| 48 | dose dial |
| 50 | proximal end 46 |
| 52 | end of 44 |
| 54 | shaft of 44 |
| 56 | threads on 54 |
| 58 | controller |
| 60 | sensing system |
| 62 | barrel |
| 64 | axis |
| 66 | spring |
| 68 | clicker |
| 69 | shoulder of housing 12 |

-continued

| Table of Drawing Numbers | |
|---|---|
| 70 | barrel flange |
| 72 | shoulder |
| 74 | barrel teeth |
| 76 | groove |
| 78 | key |
| 80 | keyway |
| 82 | tab |
| 84 | tab |
| 86 | external threads |
| 88 | drive sleeve |
| 90 | drive sleeve splines |
| 92 | housing splines |
| 94-98 | not used |
| 100 | barrel sensor system |
| 102 | sensing component |
| 104 | sensing component |
| 106 | flange out |
| 108 | shoulder |
| 110 | housing teeth |
| 112 | drive nut |
| 114 | internal thread of 112 |
| 120 | axial ridge |
| 122 | groove |
| 124-128 | not used |
| 130 | drive sleeve sensor system |
| 132 | sensing component |
| 134 | sensing component |
| 135 | modified 132 |
| 136 | key |
| 137 | keyway |
| 138 | arms |
| 140 | axial sensor |
| 142 | first sensing component |
| 144 | second sensing component |
| 146 | spaced element |
| 148 | spaced element |
| 150 | spaced element |

What is claimed is:

1. A medication delivery device, comprising:
a housing;
a dose dial movable in a spiral manner relative to said housing during dose setting from a start setting axial position to an end setting axial position in proportion to the amount of a dose set by operation of the medication delivery device,
said dose dial also being translatable, without rotation, from a start delivery axial position to an end delivery axial position in proportion to the amount of a dose delivered by operation of the medication delivery device;
a barrel rotationally coupled with said dose dial and rotatable relative to said housing during dose setting in proportion to the amount of dose set by operation of the medication delivery device, said barrel being rotatable relative to said housing from a start setting angular position to an end setting angular position during dose setting;
a drive sleeve rotatable relative to said housing during dose delivery in proportion to the amount of dose delivered by operation of the medication delivery device, said drive sleeve being rotatable relative to said housing from a start delivery angular position to an end delivery angular position during dose delivery;
an axial sensor system comprising at least one sensing component axially coupled with one of said housing and said barrel and at least one sensing component axially coupled with said dose dial, the sensing components of said axial sensor system being cooperatively configured to detect the start setting axial position and the end setting axial position and to provide start and end setting axial outputs representative of the start and end setting axial positions, respectively, the sensing components of said axial sensor system further being cooperatively configured to detect the start delivery axial position and the end delivery axial position and to provide start and end delivery axial outputs representative of the start and end delivery axial positions, respectively;

a barrel sensor system comprising a sensing component rotationally coupled with said housing and a sensing component rotationally coupled with said barrel, the sensing components of said barrel sensor system being cooperatively configured to detect the start setting angular position and the end setting angular position and to provide start and end setting angular outputs representative of the start and end setting angular positions, respectively;

a drive sleeve sensor system comprising a sensing component rotationally coupled with said housing and a sensing component rotationally coupled with said drive sleeve, the sensing components of said drive sleeve sensor system being cooperatively configured to detect the start delivery angular position and the end delivery angular position and to provide start and end delivery angular outputs representative of the start and end delivery angular positions, respectively; and a controller configured to determine from the start setting axial output, the end setting axial output, the start setting angular output, and the end setting angular output the amount of dose set by said dose dial moving from the start setting axial position to the end setting axial position, said controller also configured to determine from the start delivery axial output, the end delivery axial output, the start delivery angular output, and the end delivery angular output the amount of dose delivered by said dose dial moving from the start delivery axial position to the end delivery axial position.

2. The medication delivery device of claim 1 in which the end setting axial output is indicative of a range of positions corresponding to a number of rotations the barrel has rotated upon movement of the dose dial from the start setting axial position to the end setting axial position, and further in which the end delivery axial output is indicative of a range of positions corresponding to a number of rotations the drive sleeve has rotated upon movement of the dose dial from the start delivery axial position to the end delivery axial position.

3. The medication delivery device of claim 1 in which said controller is operable to determine from the start and end setting axial outputs a number of complete revolutions of said barrel relative to said housing during dose setting, and in which said controller is operable to determine from the start and end delivery axial outputs a number of complete revolutions of said drive sleeve relative to said housing during dose delivery.

4. The medication delivery device of claim 1 in which said controller is operable to determine from the end setting angular output and the end delivery angular output whether the barrel and drive sleeve are rotationally aligned in the same relative position after dose delivery as before dose setting.

5. The medication delivery device of claim 1 in which said controller is operable to determine the amount of dose set using only the start and end setting axial outputs and the start and end setting angular outputs, and in which said controller is operable to determine the amount of dose delivered using only the start and end delivery axial outputs and the start and end delivery angular outputs.

6. The medication delivery device of claim 1 in which one sensing component of each of said axial, barrel and drive sleeve sensor systems comprises a sensor and the other sensing component of each sensor system comprises a target, and in which each sensor is secured to said housing.

7. The medication delivery device of claim 1 in which the sensing components of said axial sensor system are further cooperatively configured to detect a zero position of said dose dial.

8. A medication delivery device, comprising:
a housing;
a dose dial having a dose configuration and a delivery configuration, in the dose configuration, the dose dial is movable in a spiral manner relative to said housing between axial positions, and in the delivery configuration, the dose dial is translatable between delivery axial positions;
a barrel coupled around the dose dial in a manner for rotation with the dose dial in the dose configuration and rotationally fixed for translatable contact with the dose dial in the delivery configuration;
a drive sleeve coupled within the dose dial in a manner for rotation with the dose dial in the delivery configuration from a start delivery angular position to an end delivery angular position;
an axial sensor system comprising a first sensing component axially coupled with one of the housing and the barrel and a second sensing component axially coupled with the dose dial, the first and second sensing components of the axial sensor system being cooperatively configured to detect and provide outputs indicative of the axial positions of the dose dial in the dose configuration and outputs indicative of the delivery axial positions of the dose dial in the delivery configuration;
a drive sleeve sensor system comprising a first sensing component coupled with the housing and a second sensing component coupled with the drive sleeve, the first and second sensing components of the drive sleeve sensor system being cooperatively configured to detect and provide outputs indicative of the start delivery angular position and the end delivery angular position; and
a controller operably connected to the axial and drive sleeve sensor systems, and, from the outputs received, configured to determine an amount of dose delivered by the dose dial when in the delivery configuration.

9. The medication delivery device of claim 8, further comprising a barrel sensor system including a first sensing component coupled with the housing and a second sensing component coupled with the barrel, the first and second sensing components of the barrel sensor system being cooperatively configured to detect and provide outputs indicative of a start setting angular position and an end setting angular position when the dose dial is in the dose configuration, and the controller operably connected to the barrel sensor system.

10. The medication delivery device of claim 9, wherein the first and second sensing components of the drive sleeve sensor system is disposed distal to the first and second sensing components of the barrel sensor system.

11. The medication delivery device of claim 9, wherein the second sensing component of the axial sensor system comprises a plurality of targets positioned axially disposed relative to one another along the dose dial.

12. The medication delivery device of claim 9, wherein the controller is operable to:
- determine from the outputs indicative of the start setting angular position and the end setting angular position a total amount of angular rotation of the barrel relative to the housing when the dose dial is in the dose configuration;
- determine from the outputs indicative of the start delivery angular position and the end delivery angular position a total amount of angular rotation of the drive sleeve relative to the housing when the dose dial is in the delivery configuration;
- determine an amount of dose set using the outputs indicative of the axial positions of the dose dial in the dose configuration and the total amount of angular rotation of the barrel; and
- determine an amount of dose delivered using the outputs indicative of the delivery axial positions of the dose dial in the delivery configuration and the total amount of angular rotation of the drive sleeve.

13. The medication delivery device of claim 1, further comprising a medication.

14. The medication delivery device of claim 8, further comprising a medication.

\* \* \* \* \*

UNITED STATES PATENT AND TRADEMARK OFFICE
CERTIFICATE OF CORRECTION

PATENT NO. : 11,471,607 B2
APPLICATION NO. : 16/321527
DATED : October 18, 2022
INVENTOR(S) : Nicola Antonio Alagia et al.

It is certified that error appears in the above-identified patent and that said Letters Patent is hereby corrected as shown below:

In the Claims

In Column 22, Line 42, in Claim 1, delete "the amount" and insert -- an amount --.

In Column 22, Line 46, in Claim 1, delete "the" and insert -- an --.

Signed and Sealed this
Fourth Day of July, 2023

Katherine Kelly Vidal
*Director of the United States Patent and Trademark Office*